United States Patent [19]

Culbert

[11] Patent Number: Plant 5,732

[45] Date of Patent: Apr. 29, 1986

[54] CHRYSANTHEMUM PLANT NAMED ILLINI PRAIRIE

[75] Inventor: John R. Culbert, Clinton, Ill.

[73] Assignee: University of Illinois, Chicago, Ill.

[21] Appl. No.: 660,057

[22] Filed: Oct. 12, 1984

Related U.S. Application Data

[63] Continuation of Ser. No. 488,012, Apr. 25, 1983, abandoned.

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Illini Prairie characterized by its flat capitulum form and single capitulum type, bright yellow spoon ray florets, 65–80 mm. diameter across face of capitulum, medium height and semi-upright branching pattern, superior floriferousness, and by its good form and color retention.

3 Drawing Figures

This is a continuation of application Ser. No. 488,012, filed Apr. 25, 1983 now abandoned.

The present invention comprises a new and distinct cultivar of *Chrysanthemum morifolium,* Ramat., named Illini Prairie.

Illini Prairie is a product of a planned breeding program which had the objective of creating new chrysanthemum cultivars with single capitulum type, yellow spoon tipped ray florets, 9 week response, and with the ability to produce commercially acceptable quality in year round pot mum programs. Such traits in combination were not present in previously available commercial cultivars.

Illini Prairie was originated from a hybridization made in a controlled breeding program in Champagne, Ill. in 1973. Illini Prairie was discovered and selected as one flowering plant within a progeny of the selected parentage by John R. Culbert in May, 1973 in a controlled environment in Champagne, Ill., and subsequently give the code number P-Ill 73-20-YS.

The first act of asexual reproduction of Illini Prairie was accomplished when vegetative cuttings were taken from the initial selection in October, 1973 in a controlled environment in Champagne, Ill. by a technician working under formulations established and supervised by John R. Culbert. Horticultural examination of selected units initiated Feb. 9, 1974 has demonstrated that the combination of characteristics as herein disclosed for Illini Prairie are firmly fixed and are retained through successive generations of asexual reproduction.

Illini Prairie has not been observed under all possible environmental conditions. The phenotype may vary significantly with variations in environment such as temperature, light intensity, and day length. The following observations, measurements and comparisons describe plants grown in Champagne and West Chicago, Ill. and Parrish, Fla. under greenhouse conditions which approximate those generally used in commercial practice.

The following traits have been repeatedly observed and are determined to be basic characteristics of Illini Prairie, which in combination distinguish this chrysanthemum as a new and distinct cultivar.

1. Flat capitulum form.
2. Single capitulum type.
3. Spoon shaped ray florets.

4. Bright yellow ray florets.
5. Diameter across the face of the capitulum 65–80 mm.
6. Medium pot plant height of about 300 mm. above the edge of pot.
7. Semi-upright branching pattern.
8. Yellow-green (immature) to yellow (mature) disc florets.
9. Good form and color retention.
10. Very floriferous.

Of the many commercial cultivars known to the present inventor, the most similar in comparison to Illini Prairie is Spice, disclosed in U.S. Plant Pat. No. 3,777. Attached is Chart A which compares certain characteristics of Illini Prairie to those same characteristics of Spice.

The accompanying photographic drawings show typical inflorescence and foliage characteristics of Illini Prairie, with colors being as nearly true as possible with illustrations of this type. Sheet 1 is a color photograph in perspective view of Illini Prairie. Sheet 2 is a close-up color photograph showing the ray florets, and sheet 3 is a black and white photo of the underside of typical foliage of Illini Prairie, at various stages of growth.

The flower color in both the perspective and close-up views do not precisely show true flower color. The blossoms are overexposed, and the bright yellow true flower color appears in the photographs in more golden tones than it actually is. However, the color values specified below are correct.

In the following description color references are made to The Royal Horticultural Society Colour Chart. The color values were determined between 1:00 and 1:30 P.M. on Apr. 25, 1983 under 2000 foot candles at Parrish, Fla.

Classification:

*Botanical.*—*Chrysanthemum morifolium,* Ramat., CV ILLINI PRAIRIE.

*Commercial.*—Novelty Daisy Pot Mum.

I. INFLORESCENCE

A. Capitulum:

*Form.*—Flat; ray florets have long handles and short spoons, with spacing between rays; 30–40 rays in a single row.

*Type.*—Daisy.

*Diameter across face.*—65–80 mm. when plant is pinched.

*Number.*—10–18 flowers per plant when pinched and grown as a spray, with the number depending on season and culture; flower size is such that showy plant results even with only 10 flowers; early flowers maintain form as later flowers develop.

B. Corolla of ray florets:

*Color (general tonality from a distance of three meters).*—Bright yellow.

*Color.*—Tube 4A, spoon (upper surface), more intense 2A.

C. Corolla of disc florets:

*Color (mature).*—Yellow.

*Color (immature).*—Lime-yellow.

D. Reproductive organs:

*Androecium.*—Present disc florets only — Many.

*Gynoecium.*—Present disc and ray florets — One floret.

II. PLANT

A. General appearance: Medium short, 300 mm., when given medium treatment as recommended; slightly spreading, and strong and stiff growth habit; can be grown as a cut flower with 18–24″ stems when given 2 weeks of long days.

B. Foliage:

*Color (abaxial).*—147B.

*Color (adaxial).*—147A.

Shape.—Deeply lobed and slightly serrated.

C. Response: 8 to early 9 week; some delay in very hot periods.

CHART A

COMPARISON OF *ILLINI PRAIRIE* AND SPICE

| CULTIVAR | RAY FLORET COLOR | CAPITULUM FORM & TYPE |
|---|---|---|
| *ILLINI PRAIRIE* | Bright Yellow | Flat spoon tipped daisy |
| SPICE | Bright Yellow | Flat spoon tipped daisy |

| CULTIVAR | DIAMETER ACROSS FACE OF CAPITULUM | PLANT HEIGHT | FLOWERING RESPONSE PERIOD |
|---|---|---|---|
| *ILLINI PRAIRIE* | 75–85 mm. | medium 300 mm. | 9 weeks |
| SPICE | 70–80 mm. | medium 300 mm. | 8 weeks |

Comparisons made of plants grown as 6″ pot plants in Parrish, Florida

I claim:

1. A new and distinct cultivar of chrysanthemum plant named Illini Prairie, as described and illustrated, and particularly characterized by its flat capitulum form and single capitulum type, bright yellow spoon ray florets; 65–80 mm. diameter across face of capitulum; medium height and semi-upright branching pattern, superior floriferousness, and by its good form and color retention.

* * * * *

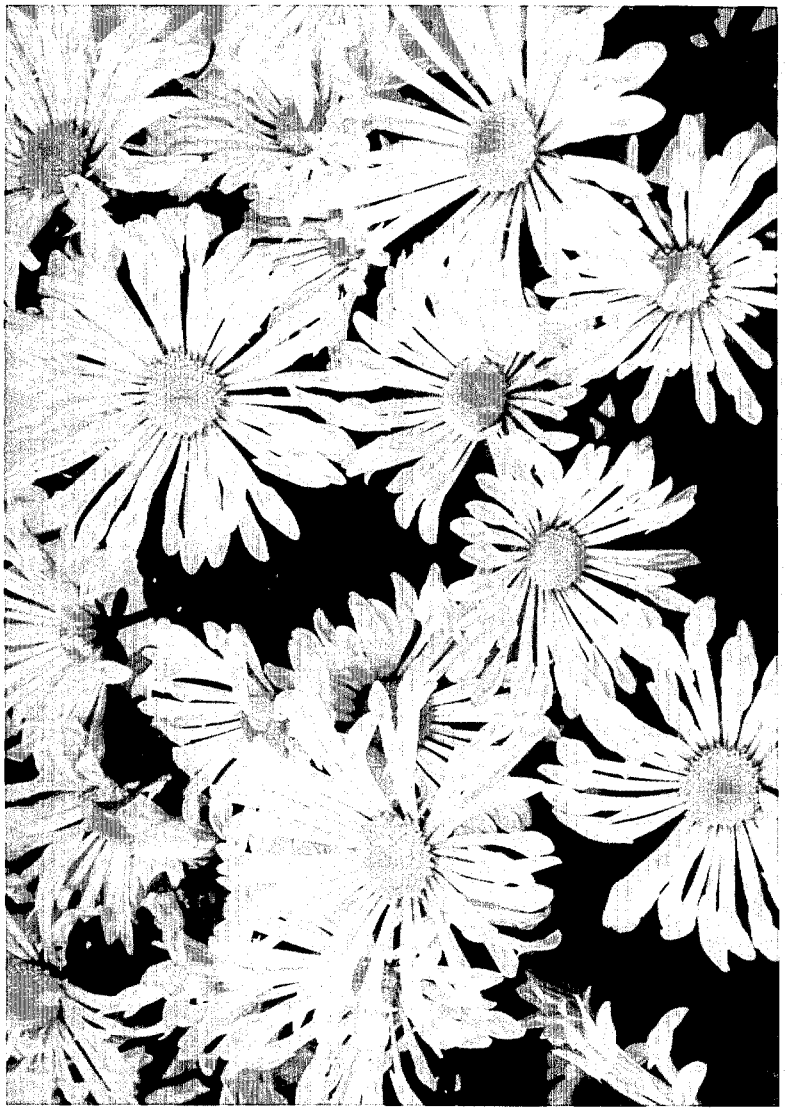

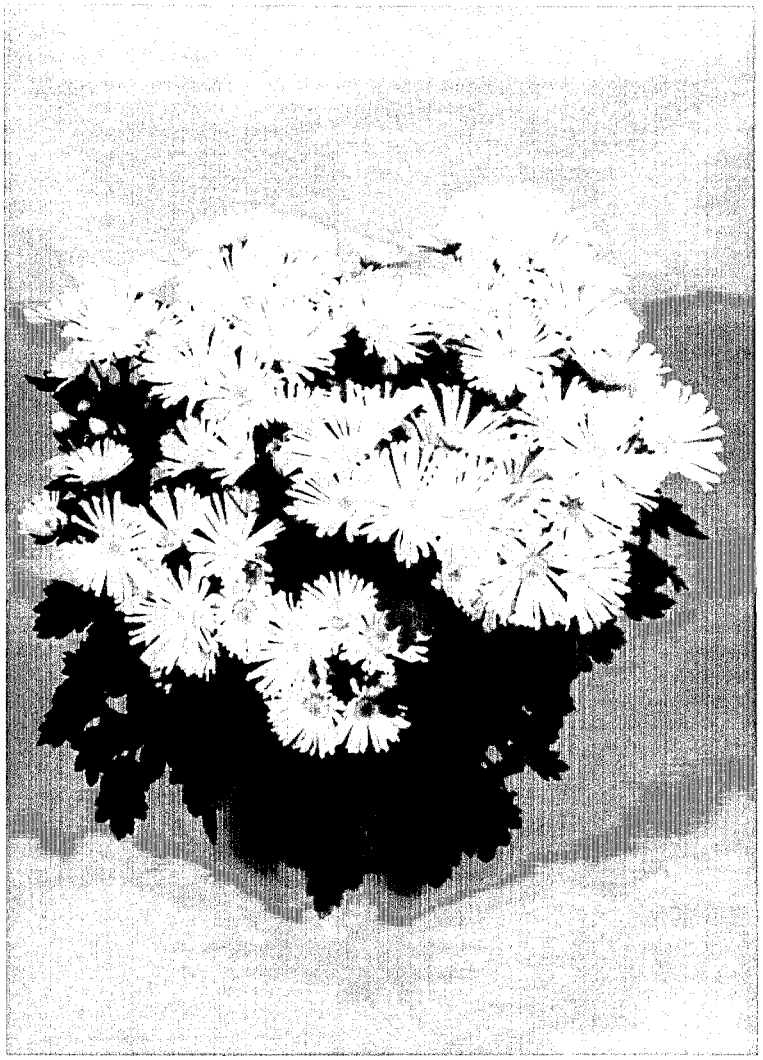

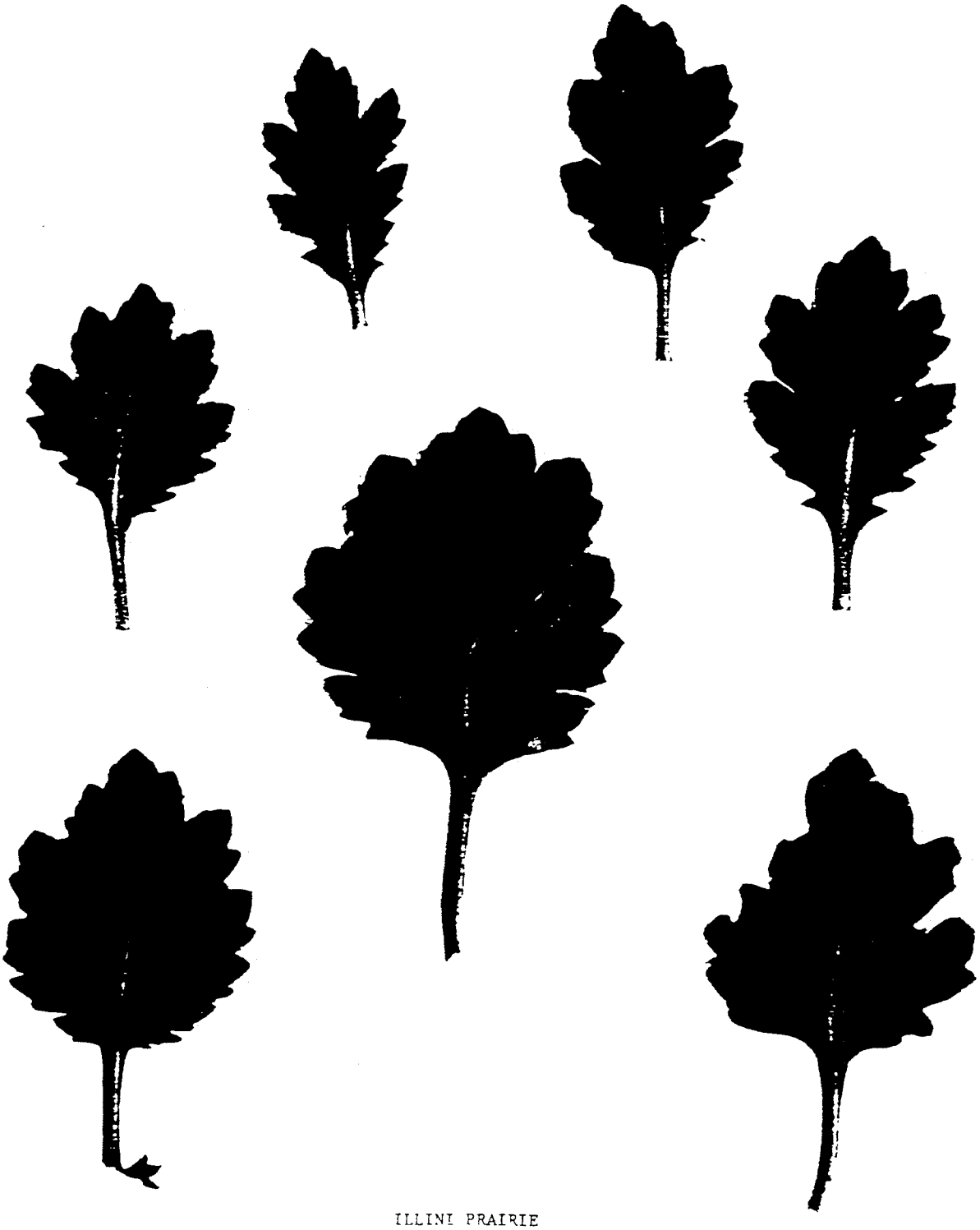
ILLINI PRAIRIE